United States Patent [19]

Asato

[11] 4,404,224

[45] Sep. 13, 1983

[54] ALKANESULFONANILIDE DERIVATIVES AND PHARMACEUTICALLY ACCEPTABLE ACID ADDITION SALTS THEREOF FOR INCREASING THE GROWTH RATE AND/OR IMPROVING THE LEAN MEAT TO FAT RATIO OF WARM BLOODED ANIMALS

[75] Inventor: Goro Asato, Titusville, N.J.

[73] Assignee: American Cyanamid Company, Stamford, Conn.

[21] Appl. No.: 326,878

[22] Filed: Dec. 2, 1981

[51] Int. Cl.³ .................... C07C 143/74; A61K 31/18
[52] U.S. Cl. ......................................... 424/321; 564/99
[58] Field of Search ........................... 564/99; 424/321

[56] References Cited

U.S. PATENT DOCUMENTS

| | | | |
|---|---|---|---|
| 3,341,584 | 9/1967 | Lareen et al. | 564/99 X |
| 3,660,487 | 5/1972 | Lareen et al. | 564/99 X |
| 3,701,808 | 10/1972 | Hartley et al. | 564/99 |
| 3,801,631 | 4/1974 | Comer et al. | 564/99 X |

OTHER PUBLICATIONS

Riggilo et al., CA 77:56558v (1972).

*Primary Examiner*—Thomas A. Waltz
*Attorney, Agent, or Firm*—Thomas J. Monahan

[57] ABSTRACT

A method for increasing the growth rate and/or improving the lean meat to fat ratio in farm and domestic animals. An effective amount of an alkanesulfonanilide derivative, pharmaceutically acceptable acid addition or metal salt thereof is administered either orally or parenterally to animals. Novel 2'hydroxy-5'-[1-alkoxy-2-(alkyl-, dialkyl- or aralkylamino)ethyl]-alkanesulfonanilides are described.

7 Claims, No Drawings

ALKANESULFONANILIDE DERIVATIVES AND PHARMACEUTICALLY ACCEPTABLE ACID ADDITION SALTS THEREOF FOR INCREASING THE GROWTH RATE AND/OR IMPROVING THE LEAN MEAT TO FAT RATIO OF WARM BLOODED ANIMALS

The invention herein described relates to a method for increasing the growth rate, enhancing the lean meat deposition and/or improving the lean meat to fat ratio in warm-blooded animals, particularly farm and domestic animals (i.e., swine, poultry, cattle, sheep, goats, rabbits, cats, dogs, etc.). The method involves either oral or parenteral administration of various alkanesulfonanilides, including novel 2'hydroxy-5'-[1-alkoxy-2-(alkyl-, dialkyl- or aralkylamino)ethyl]-alkanesulfonanilides presently revealed.

By way of background, sulfonanilide derivatives, their acid addition and metal salts are disclosed in U.S. Pat. Nos. 3,341,581 and 3,801,631. These patents reveal that the above-mentioned compounds are useful as adrenergic neurotransmitters, vasopressors, vasodepressors, analgesics, bronchodilators, $\alpha$-receptor stimulants, $\beta$-receptor stimulants, $\alpha$-receptor blocking agents, $\beta$-receptor blocking agents, papaverine-like smooth muscle depressants and anti-inflammatory agents.

In recent years the cost of raising meat animals has increased markedly in response to economic fluctuations in the areas of energy resources, ancillary products, and consumer markets. The necessity of providing adequate meat protein supplies to an expanding population is self-evident. A method for increasing the quantity and/or quality of animal protein supplies while maintaining ordinary feed requirements would facilitate delivery of required food supplies.

In light of the foregoing summary of some demands and limitations of conventional methods for the production of meat products, an improved method for quantitative and/or qualitative improvement in animal crop yields is highly desirable. An object of this invention is to provide new and useful compounds and methods of use for increasing the growth rate, enhancing the lean meat deposition and/or improving the lean meat to fat ratio in farm and domestic animals. This object is manifest in the following description and particularly delineated in the appended claims.

It has been unexpectedly discovered that oral or parenteral administration of selected sulfonanilide derivatives not only will increase the growth rates of certain warm-blooded animals but also will increase lean meat deposition and improve the lean meat to fat ratio in the bodies of these animals. In this disclosure the term lean meat is used interchangeably with the amount of muscle or protein present in referenced animals. The above-mentioned effects are achieved by oral or parenteral administration to appropriate animals of an effective amount of compounds represented by the following structural formula:

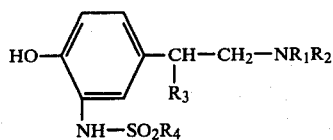

(I)

wherein $R_1$ is hydrogen or $C_1$–$C_4$ alkyl; $R_2$ is hydrogen, $C_1$–$C_4$ alkyl, benzyl, phenethyl or $\alpha,\alpha$-dimethylphenethyl; $R_3$ is OH, $OR_5$ or $SR_6$; $R_4$ is $C_1$–$C_4$ alkyl; $R_5$ is $C_1$–$C_6$ alkyl, benzyl, phenyl or allyl; and $R_6$ is hydrogen, $C_1$–$C_6$ alkyl, benzyl, phenyl or allyl; with the condition that when $R_2$ is benzyl, phenethyl or $\alpha,\alpha$-dimethylphenethyl, $R_1$ is hydrogen; and the optically active isomers and pharmacologically acceptable acid addition and metal salts thereof.

The invention herein described reveals novel formula-(I) compounds wherein $R_3$ is $OR_5$ or $SR_6$ and $R_1$, $R_2$, $R_4$, $R_5$ and $R_6$ are as described above, provided that when $R_2$ is benzyl, phenethyl or $\alpha,\alpha$-dimethylphenethyl, $R_1$ is hydrogen; and the optically active isomers and pharmaceutically acceptable acid addition and metal salts thereof. Examples of pharmaceutically acceptable acid addition compounds include the hydrochloride, sulfate, phosphate, gluconate, succinate, propionate, and similar salts.

The novel 2'hydroxy-5'-[1-alkoxy-2-(alkyl-, dialkyl- or aralkylamino)ethyl]-alkanesulfonanilides of this invention can be prepared by the following steps:

(1) reacting a 2'-hydroxy-5'-[1-hydroxy-2-(alkylamino)ethyl]alkanesulfonanilide or the dialkylamino or aralkylamino derivative thereof, with an equivalent amount or slight excess of thionyl chloride to obtain the 2'-hydroxy-5'-[1-chloro-2-(alkyl-, dialkyl- or aralkylamino)ethyl]alkanesulfonanilide hydrochloride;

(2) converting the above formed alkanesulfonanilide hydrocyloride salt to the 2'-hydroxy-5'-[1-alkoxy-2-(alkyl-, dialkyl- or aralkylamino)ethyl]alkanesulfonanilide hydrochloride by reacting the hydrochloride salt with the appropriate $C_1$–$C_6$ alcohol at temperature between about 0° to 150° C.; and (3) when a free base of an above-named hydrochloride-salt compound is desired it is obtained by neutralization of the hydrochloride salt with a suitable aqueous base (i.e., sodium hydroxide, potassium hydroxide etc.).

The 2'-hydroxy-5'-[1-alkoxy-2-(alkyl-, dialkyl- or aralkylamino)ethyl]alkanesulfonanilide derivatives and salts as well as 2'-hydroxy-5'-[1-benzyloxy-2-(alkyl-, dialkyl- or aralkylamino)ethyl]alkanesulfonanilide derivative and salts are readily prepared by the above-described procedures, and further illustrated in the following equations:

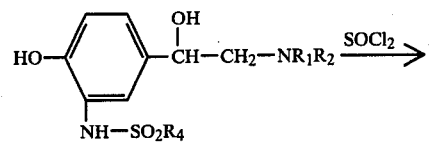

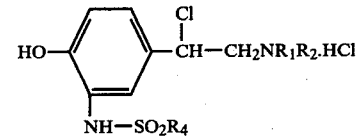

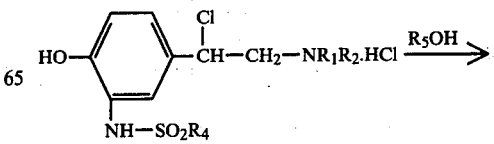

-continued

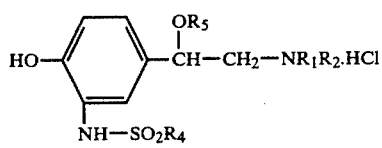

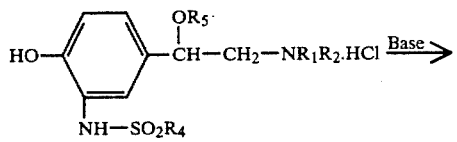

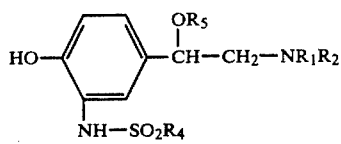

wherein $R_1$ is hydrogen or $C_1$–$C_4$ alkyl; $R_2$ is hydrogen, $C_1$–$C_4$ alkyl, benzyl, phenethyl or $\alpha,\alpha$-dimethylphenethyl; $R_4$ is $C_1$–$C_4$ alkyl and $R_5$ is $C_1$–$C_6$ alkyl, benzyl or alkyl; with the condition that when $R_2$ is benzyl, phenethyl or $\alpha,\alpha$-dimethylphenethyl, $R_1$ is hydrogen.

The 2'-hydroxy-5'-[1-phenoxy-2-(alkyl, dialkyl- or aralkylamino)ethyl]alkanesulfonanilide compounds can be prepared by reacting an appropriate 2'-hydroxy-5'-[1-chloro-2-(alkyl-, dialkyl- or aralkylamino)-ethyl]alkanesulfonanilide compounds with an excess amount (i.e., preferably 10 to 15 equivalents) of an alkali metal phenoxide in the presence of an aprotic solvent (i.e., tetrahydrofuran, ether, toluene, benzene, etc.). This reaction is carried out at a temperature between about $-5°$ and $+10°$ C. under a blanket of an inert gas.

The 2'-hydroxy-5'-[1-(alkyl-, benzyl- or allylthio)-2-(alkyl, dialkyl- or aralkylamino)-ethyl]alkanesulfonanilide compounds of the invention can be prepared by reacting an appropriate 2'-hydroxy-5'-[1-chloro-2-(alkyl-, dialkyl or aralkylamino)-ethyl]alkanesulfonanilide hydrochloride with an equimolar or excess amount of an alkyl, benzyl or allylmercaptan (i.e., $R_6SH$).

This reaction is illustrated by the following equation:

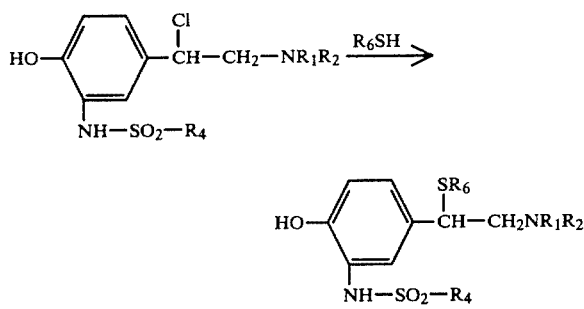

wherein $R_1$ is hydrogen or $C_1$–$C_4$ alkyl, $R_2$ is hydrogen, $C_1$–$C_4$ alkyl, benzyl, phenethyl or $\alpha,\alpha$-dimethylphenethyl; $R_4$ is $C_1$–$C_4$ alkyl; $R_6$ is hydrogen, $C_1$–$C_6$ alkyl, benzyl, or allyl. This reaction is generally conducted in the presence of an aprotic solvent (i.e., a chlorinated hydrocarbon such as ether or other similar material) at a temperature ranging from $-5°$ to $50°$ C. under a blanket of an inert gas.

2'-hydroxy-5'-[1-phenylthio-2-(alkyl-, dialkyl- or aralkylamino)ethyl]alkanesulfonanilides can be prepared by reacting an appropriate 2'-hydroxy-5'-[1-chloro-2-(alkyl-, dialkyl- or aralkylamino)ethyl]alkanesulfonanilide compound with an excess amount of an alkali metal thiophenoxide (i.e., sodium or potassium thiophenoxide) in an aprotic solvent (i.e., tetrahydrofuran, benzene, toluene or ether) at a temperature ranging from about $-5°$ to $10°$ C. under a blanket of an inert gas.

The formula-(I) compounds of this invention can generally be administered either orally or parenterally to domestic or farm animals with resultant increases in growth rates and enhancement of the lean meat to fat ratio in these animals. In actual practice the formula-(I) alkanesulfonanilides may be directly mixed with animal feeds or prepared in the form of an animal feed premix, concentrate, or supplement which can be blended with or applied as a top dressing to animal feeds. Regardless of the procedure selected, the active compound should be present at levels from about 0.05 to 500 ppm and preferably 0.1 to 100 ppm in the feed.

Animal feed premixes, supplements or concentrates can be prepared by mixing on a weight basis about 0.5 to 50% of a suitable formula-(I) alkanesulfonanilide with about 50 to 99.5% of an edible diluent. Diluents suitable for use in the manufacture of animal feed supplements, concentrates and premixes, include the following: corn meal, soybean meal, bone meal, alfalfa meal, cottonseed oil meal, urea, molasses and other similar materials. Use of the diluents in feed supplements, concentrates and premixes, improves uniformity of distribution of the active ingredient in the finished feed.

Feeds for swine, cattle, sheep and goats preferably contain about 0.05 to 400 grams of active ingredient per ton of feed, with an optimum level of about 0.25 to 100 grams per ton. Preferred poultry and domestic pet feeds range from about 0.05 to 400 grams; and most preferably 0.2 to 100 grams of active ingredient per ton of feed.

When parenteral administration is desired, formula-(I) alkanesulfonanilides may be formulated as pastes or pellets and administration to the animals by subcutaneous injection. This procedure involves injection of a formula-(I) alkanesulfonanilide derivative in an amount sufficient to provide the animal with 0.001 to 100 mg/kg of body weight/day of the active compound. The preferred dosage for swine, cattle, sheep and goats ranges from about 0.0001 to 50 mg/day/kg of body weight of the active alkanesulfonanilide derivative. The preferred dosage for poultry and domestic pets ranges from about 0.001 to 10 mg/day/kg of body weight.

Paste formulations suitable for subcutaneous injection can be prepared by dispersing a formula-(I) alkanesulfonanilide derivative in an pharmaceutically acceptable oil (i.e., peanut oil, corn oil, sesame oil, etc.). Pellets for subcutaneous injection can be prepared by mixing a formula-(I) alkanesulfonanilide derivative with a suitable diluent (i.e., carbowax, carnauba wax, etc.). A lubricant (i.e., magnesium or calcium stearate) can be added to improve the pelleting process.

In order to obtain the drug dosage levels necessary to achieve desired results (i.e., increase in growth rates and improvement in lean meat to fat rates) it may be necessary to administer multiple pellets. Also, implants may be made periodically during treatment periods in order to maintain proper animal drug levels.

In addition to effects on growth rates and lean meat to fat ratios, administration of formula-(I) alkanesulfonanilides to meat-producing animals frequently results in enhanced efficiency of feed utilization. With the use of materials and methods revealed in the present invention, producers can market superior quality meat animals in a short period of time while incurring minimum feed costs.

The following non-limiting examples further serve to illustrate the invention.

EXAMPLE 1

Preparation of 2'-Hydroxy-5'-[1-chloro-2-(isopropylamino)ethyl]methanesulfonanilide hydrochloride A 1 g sample of 2'-hydroxy-5'-[1-hydroxy-2-(isopropylamino)ethyl]methanesulfonanilide is added to 2 ml of ice-cold thionyl chloride. The mixture is then stirred at ambient temperature until the reaction is completed. Excess thionyl chloride is removed in vacuo and the residue is washed with ethyl ether thus yielding the product compound.

The compound 2'-hydroxy-5'-[1-chloro-2-(isopropylamino)ethyl]-methanesulfonanilide hydrochloride can also be prepared by heating 1 g of 2'-hydroxy-5'-[1-hydroxy-2-(isopropylamino)ethyl]methanesulfonanilide in 10 ml of dry acetonitrile or dry dimethoxyethane containing 2 ml of thionyl chloride at reflux temperature for 10 minutes following the procedure described in Journal of Medicinal Chemistry, 19, 632 (1976).

EXAMPLE 2

Preparation of 2'Hydroxy-5'-[1-ethoxy-2-(isopropylamino)ethyl]methanesulfonanilide hydrochloride A 1 g sample of 2'-hydroxy-5'-[1-chloro-2-(isopropylamino)ethyl]methanesulfonanilide hydrochloride is added to 10 ml of absolute ethanol and heated at reflux for 30 minutes. The mixture is evaporated to dryness and the residue is washed with ethyl ether thus yielding the product compound.

Neutralization of the 2'-hydroxy-5'-[1-ethoxy-2-(isopropylamino)ethyl]methanesulfonanilide hydrochloride salt with aqueous sodium hydroxide yields the free base of this compound, which can be separated from the aqueous solution and readily converted to other acid salts by titration.

EXAMPLE 3

Preparation of Chloro Intermediates

Several chloro intermediates can be prepared by the method of Example 1 as illustrated in the following equation:

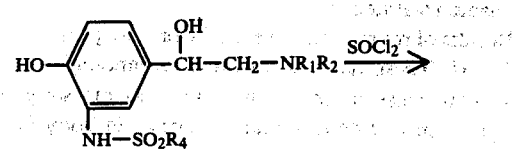

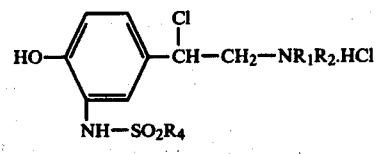

wherein substituents are:

| R$_1$ | R$_2$ | R$_4$ |
| --- | --- | --- |
| H | t-butyl | methyl |
| H | n-propyl | methyl |
| H | i-propyl | n-butyl |
| methyl | methyl | methyl |
| H | benzyl | methyl |
| H | t-butyl | n-propyl |
| ethyl | ethyl | methyl |
| H | phenethyl | methyl |
| H | α,α-dimethylphenethyl | methyl |

EXAMPLE 4

Preparation of Ethers

Several ethers can be prepared according to the method of Example 2 as illustrated in the following equation:

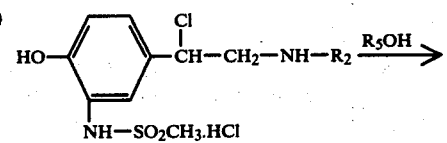

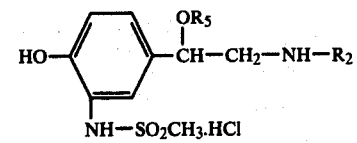

wherein substituents are:

| R$_2$ | R$_5$ |
| --- | --- |
| isopropyl | methyl |
| isopropyl | benzyl |
| isopropyl | allyl |
| t-butyl | ethyl |
| isopropyl | isopropyl |
| phenethyl | ethyl |
| α,α-dimethylphenethyl | methyl |
| α,α-dimethylphenethyl | ethyl |
| isopropyl | n-butyl |
| isopropyl | n-hexyl |

EXAMPLE 5

Preparation of 2'-Hydroxy-5'-[phenoxy-2-(isopropylamino)ethyl]methanesulfonanilide A 3.25 g sample of 2'-hydroxy-5'-[1-chloro-2-(isopropylamino)ethyl]methanesulfonanilide hydrochloride is slowly added to 45 g of sodium phenoxide in 150 ml of dry tetrahydrofuran at 0° to 5° C. under N$_2$ atmosphere. The mixture is stirred for 24 hours at ambient temperature and then poured on ice whereafter the crude product compound is separated.

EXAMPLE 6

Preparation of 2'-Hydroxy-5'-[1-phenylthio-2-(isopropylamino)ethyl]-methanesulfonanilide The compound 2'-hydroxy-5'-[1-phenylthio-2-(isopropylamino)ethyl]methanesulfonanilide can be prepared following the method described in Example 5 with the substitution of sodium thiophenoxide for sodium phenoxide.

EXAMPLE 7

Preparation of 2'-Hydroxy-5'[1-methylthio-2-(isopropylamino)ethyl]-methanesulfonanilide A 1 g sample of 2'-hydroxy-5'-[1-chloro-2-(isopropylamino)ethyl]methanesulfonanilide hydrochloride is slowly added to 5 ml of methylmercaptan in 25 ml of ethylene dichloride at 0° to $-10°$ C. under $N_2$ atmosphere. This mixture is first stirred several hours at ice-bath temperature and then stirred at ambient temperature for 24 hours. The mixture is filtered. The filter cake is washed with ethylene dichloride, added to water, and basified with 10% NaOH solution to pH 10 in an ice bath. The aqueous mixture is extracted several times with methylene chloride. The combined extracts are dried over $MgSO_4$ and evaporated to dryness thus yielding the crude product compound.

EXAMPLE 8

Several thioethers can be prepared using the method of Example 7 as illustrated in the following equation:

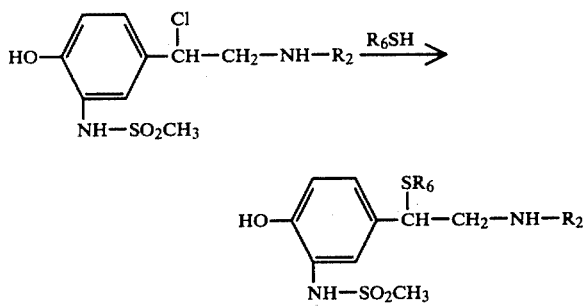

wherein substituents are:

| $R_2$ | $R_6$ |
|---|---|
| isopropyl | isopropyl |
| isopropyl | benzyl |
| t-butyl | methyl |
| phenethyl | methyl |
| α,α-dimethylphenyl | methyl |
| isopropyl | ethyl |
| isopropyl | allyl |

Use of NaSH in place of $R_6SH$ without further basification yields:

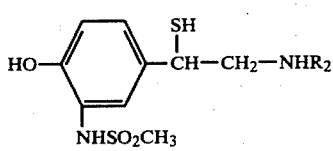

EXAMPLE 9

Evaluation of test compounds for increasing the growth rate of animals and enhancing the lean meat to fat ratio thereof by reducing fat deposition in said animals and increasing the lean meat thereof CIF female mice from Carworth Farms are received when they are six weeks old. They are housed ten to a cage in air-conditioned rooms (22° C. to 25° C.) with automatic diurnal illumination (14 hours light and 10 hours dark). Compounds of the invention are added to a basic diet of Purina Laboratory Chow which is supplied ad libitum and contains the following ingredients:

TABLE I

| Description of Diet | |
|---|---|
| (A.) Guaranteed Analysis | |
| Crude protein not less than | 23.0% |
| Crude fat not less than | 4.5% |
| Crude Fiber not more than | 6.0% |
| Ash not more than | 9.0% |
| (B.) Ingredients | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum. | |

Various experimental treatments are randomly assigned to mice cages. Each treatment is tested with three replicates, i.e., in three cages of ten mice each. There are ten control cages each of which contains ten mice. Drugs are mixed in the diet at the dosage level indicated. Feed and water are offered ad libitum over a 12-day test period. Feed spilled is collected during the test period. At the end of the experiment the collected feed is weighed and the means feed consumption per cage of ten mice is determined for each treatment. The mice are weighed as a group of ten and the weight gain is determined. The mice are sacrificed by cervical dislocation. The right uterine fat pad of each mouse is removed. The fat pads for each cage of ten mice are weighed as a unit.

A correlation between the reduction in fat pad weights of treated animals and reduction in total body fat of treated animals has been previously established. This relationship was established using several treatment groups in which the total body fat of treated animals was determined and found to correlate closely with reduction in fat pad weights of animals receiving the same treatment.

Results of representative experiments are presented in Table II. These data indicate that compounds of the invention cause increases in growth as measured by weight gain and concomitant decreases in body fat of experimental animals.

TABLE II

Evaluation of Test Compounds for Growth Enhancement and Reduction of Fat Pad Weight in Mice

| Compound | Level in Diet (ppm) | Gain (g) | % ± Control | Fat Pad Wt % ± Control |
|---|---|---|---|---|
| HO—⟨⟩—CH$_2$—NH—CH(CH$_3$)$_2$·HCl, NHSO$_2$CH$_3$, OH | 200 | 15.3 | + 27.5 | −26.3 |
| | 100 | 17.0 | + 41.7 | −24.5 |
| | 50 | 15.5 | + 29.2 | −7.1 |
| | 25 | 11.7 | + −2.5 | −19.9 |
| | 12 | 12.2 | + +1.7 | −12.8 |
| | 6 | 11.7 | + −2.5 | −11.3 |
| HO—⟨⟩—CH—CH$_2$—NH—C(CH$_3$)$_2$—CH$_2$—⟨⟩·HCl, NHSO$_2$CH$_3$, OH | 200 | 17.3 | + 44.3 | −51.1 |
| | 100 | 12.9 | + 7.5 | −36.9 |
| | 50 | 15.5 | + 29.2 | −25.5 |
| | 25 | 12.1 | + 0.8 | −13.2 |
| | 12 | 13.5 | + 12.5 | +4.2 |
| | 6 | 15.1 | + 25.8 | −7.0 |

What is claimed is:

1. A compound having the structural formula:

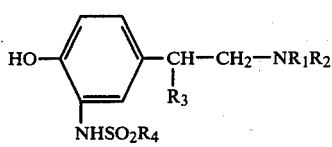

wherein $R_1$ is hydrogen or $C_1$-$C_4$ alkyl; $R_2$ is hydrogen, $C_1$-$C_4$ alkyl, benzyl, phenethyl or α,α-dimethylphenethyl; $R_3$ is $SR_6$, wherein $R_6$ is hydrogen, $C_1$-$C_6$ alkyl, benzyl, phenyl or allyl; $R_4$ is $C_1$-$C_4$ alkyl; with the condition that when $R_2$ is benzyl, phenethyl or α,α-dimethylphenethyl, $R_1$ is hydrogen; and the optically active isomers, and the pharmaceutically acceptable acid addition and metal salts thereof.

2. A method for increasing the growth rate and the lean meat to fat ratio of warm-blooded animals comprising administering either orally or parenterally to animals a growth-promoting and lean-meat-enhancing amount of a compound having the formula:

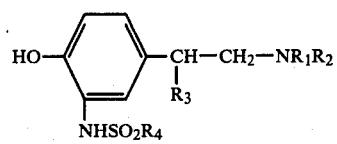

wherein $R_1$ is hydrogen or $C_1$-$C_4$ alkyl; $R_2$ is hydrogen, $C_1$-$C_4$ alkyl, benzyl, phenethyl or α,α-dimethylphenethyl; $R_3$ is OH, $OR_5$ or $SR_6$; $R_4$ is $C_1$-$C_4$ alkyl; $R_5$ is $C_1$-$C_6$ alkyl, benzyl, phenyl or allyl; $R_6$ is hydrogen, $C_1$-$C_6$ alkyl, benzyl, phenyl or allyl; with the proviso that when $R_2$ is benzyl, phenethyl, or α,α-dimethylphenethyl, $R_1$ is hydrogen; and the optically active isomers, and the pharmaceutically acceptable acid addition and metal salts thereof.

3. A method according to claim 2 wherein $R_3$ is OH; $R_1$, $R_2$ and $R_4$ are as described in claim 2, and the pharmaceutically acceptable acid addition and metal salts thereof.

4. A method according to claim 2 wherein $R_3$ is $OR_5$; $R_1$, $R_2$, $R_4$ and $R_5$ are as described in claim 1, and the pharmaceutically acceptable acid addition and metal salts thereof.

5. A method according to claim 2 wherein $R_3$ is $SR_6$; $R_1$, $R_2$, $R_4$, and $R_6$ are as described in claim 2 and the pharmaceutically acceptable acid addition and metal salts thereof.

6. A method according to claim 2 wherein the compound is 2-hydroxy-5'-[1-hydroxy-2-(isopropylamino)ethyl]methanesulfonanilide hydrochloride.

7. A method according to claim 2 wherein the compound is 2'-hydroxy-5'-[2-[(α,α-dimethylphenethylamino]-1-hydroxyethyl methanesulfonanilide hydrochloride.

* * * * *